United States Patent [19]
Bodenger

[11] 3,938,615
[45] Feb. 17, 1976

[54] STETHOSCOPE CONSISTING OF A STETHOSCOPE CHEST PIECE AND A SOUND MIXER

[76] Inventor: Jacob Bodenger, 3564 Chimney Swift Drive, Huntingdon Valley, Pa. 19006

[22] Filed: July 11, 1974

[21] Appl. No.: 487,590

[52] U.S. Cl. .............................. 181/131; 181/137
[51] Int. Cl.² ........................................ A61B 7/02
[58] Field of Search ........................... 181/131, 137

[56] References Cited
UNITED STATES PATENTS

| | | | |
|---|---|---|---|
| 1,708,398 | 4/1929 | Pilling | 181/131 |
| 2,505,124 | 4/1950 | Lepeschkin | 181/131 |
| 3,343,628 | 9/1967 | Shlyakhter et al. | 181/137 |
| 3,690,404 | 9/1972 | Collins | 181/131 |

FOREIGN PATENTS OR APPLICATIONS

| | | | |
|---|---|---|---|
| 812,103 | 8/1951 | Germany | 181/131 |
| 845,688 | 8/1952 | Germany | 181/131 |
| 321,871 | 11/1929 | United Kingdom | 181/131 |

Primary Examiner—Stephen J. Tomsky
Attorney, Agent, or Firm—Paul & Paul

[57] ABSTRACT

An improved stethoscope for use in medical diagnosis as a listening device to detect sounds within the thoracic cavity is provided having improved sound reception and transmission characteristics. The improved stethoscope has an improved stethoscope chestpiece which has two sound chambers for receiving sounds as the instrument is placed against a patient. One sound chamber is the same as that described in my earlier U. S. Pat. No. 3,067,833, utilizing a diaphragm across the mouth of the sound chamber, while the second sound chamber utilizes no diaphragm. The structure forming the second sound chamber is rotatable with respect to the structure forming the first sound chamber; rotation of the second structure with respect to the first structure between two stops results in the two chambers being acoustically connected at one position while at the second position the two chambers are acoustically insulated from each other. Dual sound transmission passageways are utilized for providing the physician with stereophonic sounds at all times. A sound mixing block is also provided which the stethoscope user may utilize at his option to provide an increased stereophonic effect and to provide a greater richness to the sound.

15 Claims, 4 Drawing Figures

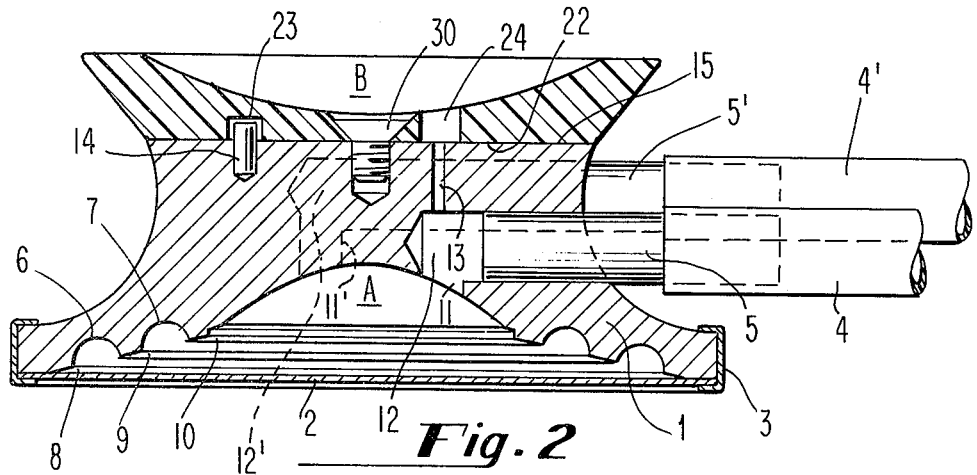
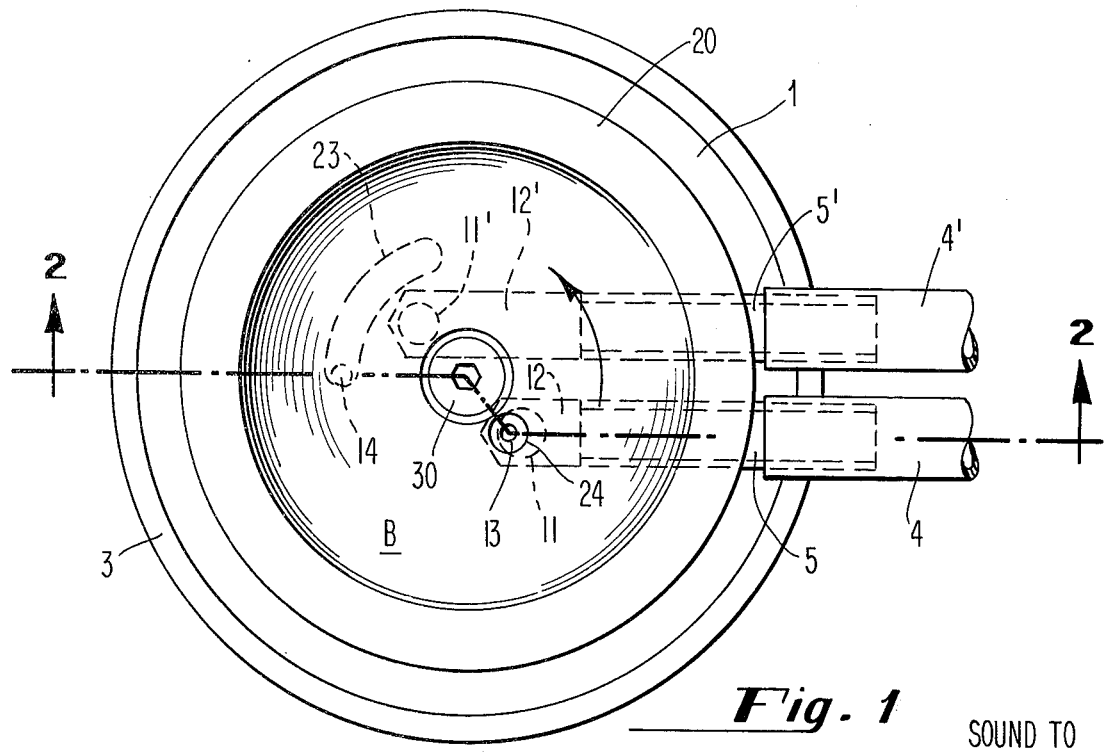
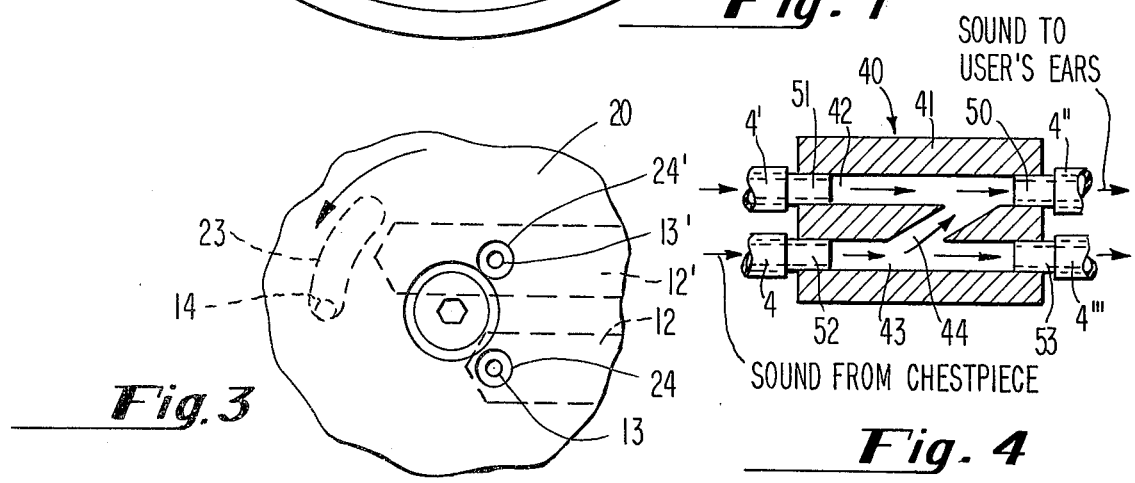

STETHOSCOPE CONSISTING OF A STETHOSCOPE CHEST PIECE AND A SOUND MIXER

BACKGROUND OF THE INVENTION

This invention relates to stethoscopes utilized in medical diagnosis and more particularly it relates to a novel stethoscope having a new stethoscope chest piece, which has characteristics greatly improved over the characteristics of stethoscopes known heretofore, and having a sound mixer. This invention specifically relates to a further improved stethoscope having improved characteristics over those found in my previous stethoscope chestpiece invention as described in U.S. Pat. No. 3,067,833, issued to me. The user of the invention can, at his option, employ a sound mixing block which when used in conjunction with the improved stethoscope chest piece provides the most greatly improved characteristics over those found in stethoscopes known heretofore. For his investigation of a variety of normal and abnormal sounds produced within the human body, the physician relies in large measure upon listening to these sounds with a stethoscope. Of particular importance are the characteristics of the heart sounds, heart murmurs, breath sounds and rales. The presence of any one of several types of lesions in or near the valves of the heart give rise to eddies in the blood flow. Such eddies result in abnormal sounds known as murmurs. Murmurs are important in the diagnosis of several conditions such as mitral stenosis, which is a narrowing of the left atrioventricular orifice. Rales are those sounds produced by the passage of air through portions of the bronchial tree which have been narrowed or which contain fluid and debris.

All the aforementioned sounds consist of mixtures of tones of different frequencies and intensities. Each sound consists of the fundamental tone, which is the note of lowest pitch, and a number of higher-pitched tones called the overtones. The tonal quality of a sound is determined by the number of overtones present, the frequencies of the overtones and their relative intensities. Generally, the more overtones present, the richer the tone color or tone quality. To reproduce sound faithfully, an instrument must be capable of transmitting all frequencies involved and must transmit them at an adequate intensity.

It is well known that the standard stethoscope does not transmit all sound frequencies and that it cannot amplify sound. Therefore it cannot transmit all overtones and cannot faithfully reproduce the sounds which come from the heart and lungs in all their natural color. Additionally, the standard stethoscope does not generally provide for the stereophonic transmission of two separate sounds from the sound chamber. The usual practice is to transmit the sound coming from the sound chamber through a single tube for a distance of about two feet. After that distance has been traversed, the tube is split at a "Y" joint with the two separate tubes each carrying the sounds of one of the stethoscope user's ears. Such non-stereophonic or monaural sound transmission provides the same sound of each of the physician's ears; this does not provide for an optimum transmission of the sound of interest. For these reasons, the conventional stethoscope has fallen into disrepute as a diagnostic instrument for discerning pathologic changes in body structures.

When a sound is initiated in a large empty room, the persistence of that sound is most striking; this phenomenon being that of reverberation and being caused by multiple echo reflections repeated in rapid succession within a closed space in which there is little absorption of sound energy. In the conventional diaphragm-type chest piece, just such a closed space exists as a sound chamber in which sound waves initiated by diaphragmatic excursion travel to the walls of the sound chamber and are reflected back and forth at random. Because the surfaces of the sound chamber are polished and hard and non-porous, absorption of sound is poor, and sound energy tends to build up as reverberation. Reverberation also tends to be more extensive in smaller chambers because reflections follow one another more rapidly. Reverberation time in the ordinary chest piece tends to be high, and as a result there is confusion between tones being perceived by the stethoscope user and the echo reflections of the preceding tones that the stethoscope user has already heard. Moreover, muddling, indistinctness and lack of intelligibility of the sounds are additional problems present in the conventional stethoscope.

My earlier improved stethoscope, as described in U.S. Pat. No. 3,067,833, had improved sound reception and transmission characteristics. These improved sound reception and transmission characteristics, via the diaphragm enclosed chamber of my invention described in U.S. Pat. No. 3,067,833, were particularly an improvement in the sound range from approximately 90 to 2,000 cycles per second (CPS).

The present invention utilizes a portion of the structure of my previous invention and also incorporates a new, second sound chamber. The new, second sound chamber used in my present invention has improved sound reception and transmission characteristics, particularly in the range of approximately 20 to 90 CPS. Accordingly, the present invention, by utilizing two optionally selected and optionally acoustically interconnected sound chambers, provides a stethoscope having improved sound reception and transmission characteristics for sounds occuring in the range of approximately 20 to 2,000 CPS.

The present invention in one of its embodiments also provides for separate stereophonic transmission of sound from the sound chamber to each of the stethoscope user's ears, thus overcoming the mixed sound characteristics of previous stethoscopes which transmitted the same sound via a single tube, with a "Y" shaped split, to the stethoscope user's two ears. The present invention in another of its embodiments further provides for transmission of two slightly different acoustic images, one to each of the stethoscope user's ears, thus creating a stereophonic effect. This is in contrast to the ordinary stethoscope which transmits only one acoustic image, via a single tube with a "Y" shaped split to the two ears of the stethoscope user.

In yet another embodiment of the present invention there is provided a sound mixing block which is optionally useable with either of the improved stethoscope chestpieces of the present invention. When the sound mixing block is used, the stethoscope user receives the richest and most intense sounds from the patient.

It is therefore an object of this invention of provide an improved stethoscope utilizing an improved stethoscope chestpiece which is capable of intensifying sound.

It is another object of this invention to provide such a chest piece which will increase the distinctiveness of a plurality of different sounds.

It is another object of this invention to provide such a chest piece which will provide increased resolution and clarity of the transmitted sounds.

It is another object of this invention to provide such a chest piece which is capable of faithfully transmitting sound having an extremely broad range of frequencies.

It is another object of this invention to provide such a chest piece which has two sound chambers.

It is another object of this invention to provide such a chest piece which has one sound chamber designed for excellent reception and transmission of sounds in the 20 to 90 CPS range and a second sound chamber designed for excellent reception and transmission of sounds in the 90 to 2,000 CPS range.

It is yet another object of this invention to provide such a chest piece, incorporating all of the objects recited above, which further provides a facility for a stereophonic transmission of sounds from the sound chambers of the chest piece to the stethoscope user's two ears via two separate sound transmission tubes.

It is yet another object of this invention to provide a chest piece, incorporating all of the objects recited above, wherein the two sound chambers are optionally selectable and wherein acoustic connection or insulation of the two sound chambers, one to another, is optionally selectable.

It is another object of this invention to provide a sound mixing apparatus which permits a portion of the sounds traveling through two separate passageways leading from a stethoscope chest piece to the stethoscope user's ears to be mixed together thus providing an increased stereophonic effect and improving the depth of the sound perceived by the stethoscope user.

It is another object of this invention to accomplish the object set forth immediately above wherein the sound mixing apparatus is optionally useable by the stethoscope user.

Other objects and advantages of this invention will be apparent to those of ordinary skill in the art from the following specification and brief description of the drawings.

BRIEF DESCRIPTION OF THE DRAWINGS

FIG. 1 is a top view of the improved stethoscope chest piece of the present invention.

FIG. 2 is a sectional view of the improved stethoscope chest piece of the present invention taken along section 2—2 indicated in FIG. 1.

FIG. 3 is a fragmentary top view of an alternative embodiment of the improved stethoscope chest piece of the present invention.

FIG. 4 is a sectional view of the sound mixing block of the present invention.

DESCRIPTION OF THE PREFERRED EMBODIMENT OF THE IMPROVED STETHOSCOPE CHEST PIECE

Referring now to FIGS. 1 and 2, there is shown a top view of the improved stethoscope chest piece of the present invention, where the complete chest piece has a generally circular configuration. The main portion of the improved stethoscope chest piece of the present invention is comprised primarily of two solid body portions, a first solid body portion 1 and a second solid body portion 20. A retaining snap ring 3 is employed to retain a solid discoid diaphragm 2, which is not visible in FIG. 1, in a substantially fixed position with respect to the first solid body portion 1. First and second sound transmission passageways 12 and 12' are formed in the first solid body portion 1. First and second hollow tubular extension members 5 and 5' are press-fitted into sound transmission passageways 12 and 12'. The conventional sound tubes 4 and 4' lead to a conventional stethoscope ear piece apparatus which is not shown. Apertures 11 and 11' are the intersection of the first and second sound transmission passageways 12 and 12' with the parabolodial surface of the sound chamber A. It is to be understood that in accordance with the stethoscope chest piece of the present invention there is no acoustic interconnection between the sound passage formed by the second sound transmission passageway 12', the hollow tubular extension member 5' and the sound tube 4'. Specifically, once sound waves enter sound chamber A and begin to travel to the ears of the physician via these two paths, there is no mixing of the sound waves traveling in one passage with the sound waves traveling in the second passage; the user of the stethoscope receives the sounds stereophonically.

A third sound transmission passageway 13 formed in the first solid body portion 1 serves to acoustically connect the first sound transmission passageway 12 with the planar surface 15 of the first solid body portion 1.

The second solid body portion 20 has a bell shaped concave recess which forms sound chamber B. A fourth sound transmission passageway 24 in the second body portion 20 provides for transmission of sound from sound chamber B to the planar surface 22 of the second solid body portion 20. Planar surface 22 of the second solid body portion is co-planar with the planar surface 15 of the first solid body portion 1. An appropriate screw 30 secures the two solid body portions 1 and 20 together. However, it is to be understood that the torque applied to screw 30 is chosen so as to tighten screw 30 only to a degree where movement of the second solid body portion 20 with respect to the first solid body portion 1 is permitted. It is to be further understood that such movement is of a rotational nature about the screw 30 as indicated by the arrow in FIG. 1. Such movement occurs in response to an external torque applied by the stethoscope user, and planar surfaces 15 and 22 remain in contact before, during and after the movement. A curved groove 23 is provided in the second solid body portion 20. The groove 23 is suitably sized for receipt of a stop pin 14 which is imbedded in the first solid body portion 1 and which protrudes from planar surface 15. The combination of the curved groove 23 and the stop pin 14 act in concert with the screw 30 to limit the movement of the second solid body portion with respect to the first solid body portion 1.

It will be understood that movement of the second solid body portion 20 with respect to the first solid body portion 1, in response to an external torque applied by the stethoscope user, will be only between two (2) discrete extreme positions. These two discrete extreme positions define two optionally selectable configurations of the stethoscope chest piece. The first configuration, designated hereinafter as "Position 1+ is the configuration illustrated by FIGS. 1 and 2 where the stop pin 14 is at the counterclockwise extremity of the curved groove 23, when the chest piece is viewed from the top, as in FIG. 1. The second configuration, designated hereafter as "Position 2" is the configuration where the stop pin 14 is at the clockwise extremity of the curved groove 23. This configuration would be achieved by turning the second solid body portion 20, in the counter-clockwise direction indicated by the arrow in FIG. 1, until the stop pin 14 contacts the clockwise extremity of the curved groove 23. It is believed that the configuration of the stethoscope chest piece of the present invention when the chest piece has achieved Position 2 is clearly described herein and that no drawing of the chest piece configured in Position 2 is necessary.

Reference is now made to FIG. 2, which shows the improved stethoscope chest piece of the present invention in even more detail. The first solid body portion 1 and the solid discoid diaphragm 2 are held in position by the retaining snap ring 3.

The structural configuration of sound chamber A, concentric grooves 6 and 7, concentric flats 8, 9 and 10, and the relationship of the solid discoid diaphragm 2, all as shown in FIG. 2, is substantially the same as revealed in my previous improved stethoscope described in my U.S. Pat. No. 3,067,833, the disclosure of which is hereby incorporated herein by reference. The stop pin 14 is force fit into a hole counterbored in the first solid body portion 1 in such a way that the stop pin 14 extends outward from the planar surface 15.

The sound chamber designated as sound chamber B is formed in an upper surface of the second solid body portion 20, starting at the paraboloidal surface of sound chamber B, for securing the second solid body portion 20 to the first solid body portion 1, via the screw means 30. The fourth sound transmission passageway, designated as 24 in the second solid body portion 20, is shown as a somewhat larger passageway than the third sound transmission passageway 13, and is shown acoustically connecting sound chamber B and the planar surface 22 of the second solid body portion 20. It is to be understood that the disparity in size of passageways 13 and 24, as shown in the drawings, is not necessary for the successful operation of the invention. Passageways 13 and 24 have been shown to be of two different diameters to aid the clarity of the drawings.

It will be noted that the spatial relationship of the third sound transmission passageway 13 and the fourth sound transmission passageway 24, when the stethoscope chest piece is in the configuration of Position 1, is shown in both FIGS. 1 and 2, with the relationship being perhaps more clearly perceived by reference to FIG. 2. In Position 1, the third sound transmission passageway 13 and the fourth sound transmission passageway 24 clearly are in acoustic communication. When the stethoscope chest piece is in Position 1, soundwaves present in sound chamber B travel through the fourth passageway 24 to the third passageway 13 and from the third passageway 13 to the first passageway 12. From the first passageway 12, some of the sound will travel to an ear of the stethoscope user via the hollow tubular extension member 5 and sound tube 4 while another portion of the sound will reach the remaining ear of the stethoscope user by traveling through sound chamber A, the second passageway 12', hollow tubular extension member 5' and sound tube 4'.

When the second solid body portion 20 has been rotated counterclockwise with respect to the first solid body portion 1 so that the stethoscope chest piece is in Position 2, it will be apparent that there is no acoustic communication between passageways 13 and 24 and that only sound chamber A is operative. The third sound transmission passageway 13 will be closed by the planar surface 15 of the first solid body portion 1. When the stethoscope chest piece is in Position 2, some of the sound in sound chamber A will travel to one of the stethoscope user's ears via the first passsageway 12, the hollow tubular extension member 5 and the sound tube 4 while another portion of sound will reach the remaining ear of the stethoscope user via the second passageway 12', the hollow tubular member 5' and the sound tube 4'. No sound from the sound chamber B will reach the stethoscope user's ears when the stethoscope chest piece is in Position 2 because in Position 2, sound chamber B is acoustically insulated from the remainder of the chest piece due to the absence of acoustic communication between passageways 13 and 24.

It will be understood that the term "acoustic communication" as used herein denotes the condition whereby the positional relationship of two passageways for the transmission of sound is such that sound waves present in one such passageway may travel directly into the second passageway via the air present in the two passageways without traveling through any solid material. Furthermore, in such a condition, there is no barrier to the free migration of air from one such passageway into the second such passageway. Likewise, it will be understood that the term "acoustic insulation" as used herein denotes the condition whereby the positional relationship of two passageways for the transmission of sound is such that sound waves present in one such passageway may not travel directly into the second passageway via the air in the two passageways but rather the sound waves are confronted with a solid barrier. Accordingly, in this condition, the solid barrier prevents the free migration of air from such a first passageway into the second such passageway.

It will also be understood that the term "acoustic insulation" as used herein is a relative term and has meaning only when used to describe a condition with respect to sound waves of a low intensity. In this context low intensity sound waves denote sound waves of the intensity occuring in either sound chamber of the stethoscope chest piece of the present invention when that chosen sound chamber is placed against a patient's body. Such low intensity sound waves cannot travel through solid structure. Accordingly, a user of the stethoscope would hear nothing if the stethoscope chest piece were configured in a position whereby the sound chamber which was placed against the patient was acoustically insulated from the sound transmission passageways leading to the stethoscope user's ears. It is further to be understood that the physician using the stethoscope will use sound chamber B for listening to body sounds when the chest piece apparatus is in Position 1 described above. He will use the diaphragm side, sound chamber A, and when the chest piece is in the above described Position 2.

DESCRIPTION OF AN ALTERNATIVE EMBODIMENT OF THE IMPROVED STETHOSCOPE CHESTPIECE

FIG. 3 is a fragmentary top view of an alternative embodiment of the present improved stethoscope chest piece invention, wherein an additional sound transmission passageway 24' is provided in the second solid body portion 20 for acoustic connection with an additional sound transmission passageway 13' provided in the first solid body portion 1. Use of this embodiment of the invention is identical to the use of the first embodiment of the invention as described above. Specifically, when the second solid body portion 20 is rotated counterclockwise (in the direction of the arrow shown in FIG. 3) from Position 1 to Position 2, upon attaining Position 2 there is no acoustic connection either between passageway 13 and passageway 24 or between passageway 13' and passageway 24'.

In either embodiment, the first solid body portion 1 and the second solid body portion 20 can be manufactured of any reasonably hard material which can be suitably molded or machined. The first solid body portion 1 has been manufactured of a steel alloy, while the second solid body portion 20 has been manufactured of a Bakelite-type material. Diaphragm 2 may conventionally be formed from any hard, thin material suitable for acoustic transmission use, such as the material known as Muscovite Mica. The remaining structural elements such as the retaining snap-ring 3, the hollow tubular extension members 5 and 5', the stop pin 14, etc., may be made of any suitable material which may be appropriately machined and formed.

DESCRIPTION OF THE SOUND MIXER

The sound mixer of the present invention is shown in a sectional view, FIG. 4. It is to be understood that the sound mixer can be used in combination with either of the embodiments of the chest piece described above and it is also to be understood that when the sound mixer is used with either embodiment of the improved chest piece, the sounds perceived by the stethoscope user will be of even greater intensity and will have even greater three dimensional, stereophonic effect than when one of the embodiments of the improved stethoscope chest piece is used without the sound mixer. Furthermore, either of the embodiments of the improved stethoscope chest piece described above can be successfully utilized without the sound mixer of the present invention and those embodiments of the improved stethoscope chest piece will still provide more accurate and higher intensity sounds than have been heretofore available from stethoscope chest pieces. These improved stethoscope chest pieces also will provide three dimensional, stereophonic sounds which have not been available heretofore. However, the most preferred embodiment of the present invention is to utilize the stethoscope chest piece described initially above with the sound mixer described herein.

The sound mixer 40 is comprised of a solid block 41 which has passageways 42 and 43 therein for transmission of sound therethrough. Hollow sound transmission tubes 50, 51, 52 and 53 of approximately the same outside diameter and formed similarly to tubes 5 and 5' extending from the stethoscope chest piece, are press fitted into the ends of the passageways 42 and 43. The hollow sound transmission tubes 50, 51, 52 and 53 in combination with passageways 42 and 43 serve to connect sound tubes 4 and 4', which come from either embodiment of the improved stethoscope chest piece described above, to sound tubes 4'' and 4''', which in turn lead to the stethoscope user's ears. A connecting passageway 44 connects passageway 42 with passageway 43. Accordingly, passageway 42 is always in acoustic communication with passageway 43. Passageway 44 permits a small portion of the sound which has entered passageway 43 from sound tube 4 to travel to passageway 43 and on to the stethoscope user's ear via sound tube 4'' while the majority of the sound in passageway 43 continues to travel to the stethoscope user's ear through sound transmission passageway 4'''. Correspondingly, a small portion of the sound which has entered passageway 42 from sound transmission tube 4' travels through passageway 44 to passageway 43 and to the stethoscope user's ear via sound transmission tube 4''', while the majority of the sound in passageway 42 travels to the stethoscope user's other ear via sound transmission tube 4''. It has been found that use of the sound mixer 40 makes the sound images perceived by the stethoscope user more clear. Use of the sound mixer 40 aids the stereophonic effect perceived by the stethoscope user.

It is also to be understood that the use of the sound mixer described herein is not limited to use in conjunction with one of two improved stethoscope chest pieces which are part of the present invention. Specifically, the sound mixer has been very successful utilized in conjunction with the dual chest piece stethoscope described in U.S. Pat. No. 3,144,091 issued to me.

It is further to be understood that the stethoscope user may utilize either embodiment of the improved stethoscope chest piece described herein, first with the sound mixer and then without the sound mixer, while examining the same patient, in order to hear the widest variety of sounds being produced within the body of the patient. It is to be understood that the sound tubes 4, 4', 4'' and 4''' are pushed onto the ends of the hollow sound transmission tubes 50, 51, and 53 of the sound mixer and that sound tubes 4 and 4' are similarly pushed onto the sound transmission extension tubes 5 and 5'. Accordingly, sound tubes 4'' and 4''' coming from a conventional stethoscope ear piece, which is not shown, can be fitted onto tubes 5 and 5' by the stethoscope user, thus providing for use of the chosen embodiment of the stethoscope chest piece without the sound mixer.

In clinical use, the herein described and claimed stethoscope chest piece has proven to transmit sounds over a greatly increased frequency range, has provided significant intensification of sound, has adequately transmitted overtones, has provided excellent resolution of body sounds, has reduced sound reverberation interference and spherical aberration, has improved transmission of low pitch, high pitch and second heart sounds, has permitted easy hearing of emphysematous chest and thick walled chest sounds and has proved to be of aid to a diagnostician whose hearing is defective. Clinical experience has shown that the sensitivity of the chest piece of this invention is increased over conventional stethoscopes with heart sounds, including gallops, being well appreciated. Low pitch murmurs of mitral stenosis are heard well. Moreover, diagnosis of breath sounds is significantly aided when use is made of the improved stethoscope chest piece of this invention.

While the preferred embodiment of this invention and an alternative embodiment have been described in some detail, it will be apparent to those of skill in the art that various modifications can be made within the scope of the present invention as defined in the appended claims.

Having thus described my invention, I claim the following:

1. An improved stethoscope chest piece having two cavities therein, each of said cavities forming respectively a first and second sound chamber in said chest piece, a first one of said two sound chambers having a flat, substantially rigid diaphragm disposed in a planar relationship with said first sound chamber so as to form a closed sound chamber, said chest piece further having means for providing for both optionally selectable acoustic insulation of said second sound chamber from said first sound chamber and optionally selectable acoustic communication of said first and second chambers.

2. An improved stethoscope chest piece comprising:
 a. a first solid body portion having a first sound chamber therein, having first and second passageways for transmission of sound therethrough, said first and second passageways providing means for acoustically connecting said sound chamber with conventional stethoscope sound tubes, said first solid body portion having a third passageway acoustically connecting said first passageway with a surface of said first solid body portion for sound transmission therebetween, said surface of said first solid body portion being complementarily configured for mating with a similarly complementarily configured surface of a second solid body portion;
 b. a second solid body portion having a second sound chamber therein, said second solid body portion having a fourth passageway therein for transmission of sound therethrough, said fourth passageway acoustically connecting said second sound chamber in said second solid body portion with a surface of said second solid body portion for sound transmission therebetween, said surface of said second solid body portion being complementarily configured for mating with said complementarily configured surface of said first solid body portion;
 c. means for securing together said first and second solid body portions, said means being adapted to provide for movement of said second solid body portion with respect to said first solid body portion in response to an externally applied force, said movement being between first and second fixed positions;
wherein said first and second solid body portions are so disposed that when said second solid body portion is at the first fixed position with respect to said first solid body portion, said third passageway in said solid body portion is in acoustic commuciation with said fourth passageway in said second solid body portion, and such that when said second solid body portion is at said second fixed position with respect to said first solid body portion, said third passageway in said first solid body portion is acoustically insulated from said fourth passageway in said second solid body portion.

3. The improved stethoscope chest piece of claim 2 wherein:
 a. said first solid body portion has a first additional passageway for transmission of sound therethrough, said additional passageway being denominated as a fifth passageway acoustically connecting said second passageway and a surface of said first solid body portion for sound transmission therebetween; and
 b. said second solid body portion has a second additional passageway for transmission of sound therethrough, said second additional passageway being denominated as a sixth passageway for transmission of sound, said sixth passageway acoustically connecting said sound chamber in said second solid body portion and a surface of said second solid body portion for sound transmission therebetween; and wherein said first and second solid body portions are so disposed that when said second solid body portion is at said first fixed position with respect to said first solid body portion, said fifth passsageway in said first solid body portion is in acoustic communication with said sixth passageway in said second solid body portion, and such that when said second solid body portion is at said second fixed position with respect to said first solid body portion, said fifth passageway in said first solid body portion is acoustically insulated from said sixth passageway in said second solid body portion.

4. The improved stethoscope chest piece of claim 2, further comprising:
 a. a thin diaphragm covering said first sound chamber in said first solid body portion; and
 b. means for retaining said diaphragm in sound transmitting relationship to said first sound chamber.

5. The improved stethoscope chest piece of claim 3, further comprising:
 a. a thin diaphragm covering said first sound chamber in said first solid body portion; and
 b. means for retaining said diaphragm in sound transmitting relationship to said first sound chamber.

6. An improved stethoscope chest piece comprising:
 a. a first solid body portion having at least three distinct exterior surfaces, a first one of said three distinct exterior surfaces having a first sound chamber therein, said first solid body portion having first and second passageways for transmission of sound therethrough, said first and second passageways acoustically connecting said first sound chamber to a second one of said three distinct exterior surfaces of said first solid body portion for sound transmission therebetween, said first solid body portion having a third passageway for sound transmission therethrough, said third passageway acoustically connecting said first passageway with said third distinct surface of said first solid body portion for sound transmission therebetween, said third distinct surface of said first solid body portion being a planar surface suitably adapted for flush mounting thereo a similar planar surface of a second solid body portion;
 b. two hollow tubular extension members extending from and in force-fit relation with said first and second passageways, said hollow tubular extension members being means for transmitting sound therethrough from said first and second passageways to first and second conventional stethoscope sound transmission tubes;
 c. a second solid body portion having at least two distinct exterior surfaces, a first one of said two distinct exterior surfaces having a second sound chamber therein, a second one of said two distinct external surfaces of said second solid body portion being a planar surface suitably adapted for flush mounting thereto a similar planar surface of said first solid body portion, said second solid body portion having a fourth passageway for transmission of sound therethrough, said fourth passageway acoustically connecting said second sound chamber in said second solid body portion to said planar surface of said second said body portion for sound transmission therebetween; and
 d. means for securing together said first and second solid body portions, said means being adapted to provide for rotational movement of said second solid body portion with respect to said first solid body portion in response to an externally applied torque, while said first and second solid body portions are secured together, said movement being between first and second fixed positions;

wherein said first and second solid body portions are so disposed that when said second solid body portion is at said first fixed position with respect to said first solid body portion, said third passageway in said first solid body portion is in acoustic communication with said fourth passageway in said second solid body portion, and such that when said second solid body portion is at said second fixed position with respect to said first solid body portion, said third passageway in said first solid body portion is acoustically insulated from said fourth passageway in said second solid body portion.

7. The improved stethoscope chest piece of claim 6, wherein there is a substantially parabolodial shaped subchamber, within said first sound chamber, in acoustic communication with said first and second passageways for transmission of sound in said first solid body portion, and wherein an annular groove is formed within said first sound chamber concentrically spaced from said subchamber, and wherein an annular flat surface present on said first solid body portion interconnects said annular groove and said subchamber in acoustical relationship wherein said flat surface forms a small, acute angle within the plane of a diaphragm, and wherein said improved stethoscope chest piece of claim 6 further comprises:
   a. a thin diaphragm covering said first sound chamber; and
   b. means for retaining said diaphragm in sound transmitting relationship to said first sound chamber.

8. The improved stethoscope chest piece of claim 7, wherein said subchamber is recessed with respect to said flat surface.

9. The improved stethoscope chest piece of claim 6, wherein:
   a. said first solid body portion has an additional passageway for transmission of sound therethrough, said additional passageway being denominated as a fifth passageway acoustically connecting said second passageway and said third distinct surface of said first solid body portion for sound transmission therebetween;
   b. said second solid body portion has a second additional passageway for transmission of sound therethrough, said second additional passageway being denominated as a sixth passageway for transmission of sound, said sixth passageway acoustically connecting said second sound chamber in said second solid body portion with said planar surface of said second solid body portion for sound transmission therebetween;
wherein said first and second solid body portions are so disposed that when said second solid body portion is at said first fixed position with respect to said first solid body portion, said fifth passageway in said first solid body portion is in acoustic communication with said sixth passageway in said second solid body portion, and such that when said second solid body portion is at said second fixed position with respect to said first solid body portion, said fifth passageway in said first solid body portion is acoustically insulated from said sixth passageway in said second solid body portion.

10. The improved stethoscope chest piece of claim 9 wherein there is a substantially parabolodial shaped subchamber within said first sound chamber in acoustic communication with said first and second passageways for transmission of sound in said first solid body portion, and wherein an annular groove is formed within said first sound chamber concentrically spaced from said subchamber, and wherein an annular flat surface present on said first solid body portion interconnects said annular groove and said subchamber in acoustical relationship wherein said flat surface forms a small, acute angle with the plane of a diaphragm, and wherein said improved stethoscope chest piece of claim 9 further comprises:
   a. a thin diaphragm covering said first sound chamber; and
   b. means for retaining said diaphragm in sound transmitting relationship to said first sound chamber.

11. The improved stethoscope chest piece of claim 10 wherein said subchamber is recessed with respect to said flat surface.

12. The improved stethoscope chest piece of claim 6 wherein said means for securing together said first and second solid body portions is adapted to provide for rotational movement of said second solid body portion with respect to said first solid body portion in response to an externally applied torque while said first and second solid body portions are secured together, and further comprises:
   a. screw means passing through said second solid body portion and rotationally engaging thread means in said first solid body portion;
   b. thread means tapped in said first solid body portion;
   c. pin means protruding from said planar surface of said first solid body portion;
   d. curved groove means in said planar surface of said second solid body portion, said curved groove means being suitably disposed for receipt of said pin means in sliding engagement, said curved groove means further being curved about a portion of a circle which if drawn would have its center coincident with the center line of said screw means; wherein said screw means, said thread means, said pin means and said curved groove means together define first and second fixed positions of said first and second solid body portions with respect to each other, said first and second fixed positions coinciding respectively with the pin means being at a first end and at a second end of said curved groove means.

13. The improved stethoscope chest piece of claim 9 wherein said means for securing together said first and second solid body portions is adapted to provide for rotational movement of said second solid body portion with respect to said first solid body portion in response to an externally applied torque while said first and second solid body portions are secured together and further comprises:
   a. screw means passing through said second solid body portion and rotationally engaging thread means in said first solid body portion;
   b. thread means tapped in said first solid body portion;
   c. pin means protruding from said planar surface of said first solid body portion;
   d. curved groove means in said planar surface of said second solid body portion, said curved groove means being suitably disposed for receipt of said pin means in sliding engagement, said curved groove means further being curved about a portion of a circle which if drawn would have its center coincident with the center line of said screw means; wherein said screw means, said thread means, said pin means and said curved groove means together define first and second fixed positions of said first and second solid body portions with respect to each other, said first and second fixed positions coinciding respectively with the pin means being at a first end and at a second end of said curved groove means.

14. The improved stethoscope chest piece of claim 2 wherein said means for securing together said first and second solid body portions is adapted to provide for rotational movement of said second solid body portion with respect to said first solid body portion in response to an externally applied torque while said first and second solid body portions are secured together and further comprises:
 a. screw means passing through said second solid body portion and rotationally engaging thread means in said first solid body portion;
 b. thread means tapped in said first solid body portion;
 c. pin means protruding from said planar surface of said first solid body portion;
 d. curved groove means in said planar surface of said second solid body portion, said curved groove means being suitably disposed for receipt of said pin means in sliding engagement, said curved groove means further being curved about a portion of a circle which if drawn would have its center coincident with the center line of said screw means;
wherein said screw means, said thread means, said pin means and said curved groove means together define first and second fixed positions of said first and second solid body portions with respect to each other, said first and second fixed positions coinciding respectively with the pin means being at a first end and at a second end of said curved groove means.

15. The improved stethoscope chest piece of claim 3 wherein said means for securing together said first and second solid body portions is adapted to provide for rotational movement of said second solid body portion in response to an externally applied torque while said first and second solid body portions are secured together and further comprises:
 a. screw means passing through said second solid body portion and rotationally engaging thread means in said first solid body portion;
 b. thread means tapped in said first solid body portion;
 c. pin means protruding from said planar surface of said first solid body portion;
 d. curved groove means in said planar surface of said second solid body portion, said curved groove means being suitably disposed for receipt of said pin means in sliding engagement, said curved groove means further being curved about a portion of a circle which if drawn would have its center coincident with the center line of said screw means;
wherein said screw means, said thread means, said pin means and said curved groove means together define first and second fixed positions of said first and second solid body portions with respect to each other, said first and second fixed positions coinciding respectively with the pin means being at a first end and at a second end of said curved groove means.

* * * * *

UNITED STATES PATENT OFFICE
CERTIFICATE OF CORRECTION

Patent No. 3,938,615　　　　　　　　　Dated February 17, 1976

Inventor(s) Jacob Bodenger

It is certified that error appears in the above-identified patent and that said Letters Patent are hereby corrected as shown below:

Column 4, line 63, " "Position 1+ " should be

--"Position 1"-- ;

Column 8, line 29, after "51" insert --52--;

Signed and Sealed this

Twelfth Day of October 1976

[SEAL]

Attest:

RUTH C. MASON  
Attesting Officer

C. MARSHALL DANN  
Commissioner of Patents and Trademarks